US010150107B2

(12) United States Patent
Iwamoto et al.

(10) Patent No.: US 10,150,107 B2
(45) Date of Patent: *Dec. 11, 2018

(54) OXYGEN-ABSORBING RESIN COMPOSITION

(71) Applicant: MITSUBISHI GAS CHEMICAL COMPANY, INC., Tokyo (JP)

(72) Inventors: Shinpei Iwamoto, Kanagawa (JP); Satoshi Okada, Hiratsuka (JP); Shinichi Ikeda, Tokyo (JP); Fumihiro Ito, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/770,934

(22) PCT Filed: Mar. 5, 2014

(86) PCT No.: PCT/JP2014/055549
§ 371 (c)(1),
(2) Date: Aug. 27, 2015

(87) PCT Pub. No.: WO2014/136811
PCT Pub. Date: Sep. 12, 2014

(65) Prior Publication Data
US 2016/0008800 A1    Jan. 14, 2016

(30) Foreign Application Priority Data

Mar. 5, 2013  (JP) ................................. 2013-042603
May 29, 2013  (JP) ................................. 2013-112674

(51) Int. Cl.
| | |
|---|---|
| *C08G 63/181* | (2006.01) |
| *B01J 31/04* | (2006.01) |
| *B01J 20/22* | (2006.01) |
| *C08G 63/127* | (2006.01) |
| *C08G 63/60* | (2006.01) |
| *B01J 20/26* | (2006.01) |
| *B01J 20/30* | (2006.01) |
| *B01J 20/28* | (2006.01) |
| *A61L 31/06* | (2006.01) |
| *A61L 31/14* | (2006.01) |
| *B01D 53/02* | (2006.01) |
| *B01D 53/81* | (2006.01) |
| *B65D 81/26* | (2006.01) |

(52) U.S. Cl.
CPC ............... *B01J 31/04* (2013.01); *A61L 31/06* (2013.01); *A61L 31/14* (2013.01); *B01D 53/02* (2013.01); *B01D 53/81* (2013.01); *B01J 20/22* (2013.01); *B01J 20/261* (2013.01); *B01J 20/262* (2013.01); *B01J 20/28042* (2013.01); *B01J 20/3007* (2013.01); *C08G 63/127* (2013.01); *C08G 63/60* (2013.01); *B01D 2251/21* (2013.01); *B01D 2255/2073* (2013.01); *B01D 2255/20738* (2013.01); *B01D 2255/20746* (2013.01); *B01D 2255/20753* (2013.01); *B01D 2255/20761* (2013.01); *B01D 2257/104* (2013.01); *B01D 2259/4525* (2013.01); *B01J 2220/46* (2013.01); *B01J 2231/70* (2013.01); *B01J 2531/004* (2013.01)

(58) Field of Classification Search
CPC .... C08G 63/181; C08G 63/127; C08G 63/19; C08G 63/60; C08G 63/64; C08G 63/916; C08G 63/54; C08G 63/00; B65D 81/266; B65D 81/267
See application file for complete search history.

(56) References Cited

U.S. PATENT DOCUMENTS

| | | | |
|---|---|---|---|
| 3,505,282 A * | 4/1970 | Storms ................. | C08G 63/181 528/180 |
| 5,346,644 A | 9/1994 | Speer et al. | |
| 6,063,503 A | 5/2000 | Hatakeyama et al. | |
| 6,527,976 B1 * | 3/2003 | Cai ........................ | C08K 5/098 252/188.28 |
| 6,653,440 B2 * | 11/2003 | Hirokane ............... | C08G 63/16 528/272 |
| 9,428,692 B2 | 8/2016 | Okada et al. | |
| 2003/0068455 A1 * | 4/2003 | Oguro ..................... | C08L 67/02 428/35.7 |

(Continued)

FOREIGN PATENT DOCUMENTS

| | | |
|---|---|---|
| EP | 2 404 948 | 1/2012 |
| EP | 2907848 | 9/2013 |

(Continued)

OTHER PUBLICATIONS

Eastar Tech Data , Eastman , Feb. 2012.*
Matthew G. McKee et al "Branched polyesters: recent advances in synthesis and performance", 2005,pp. 507-509.*
Search Report issued by PCT/JP2014/055549 patent office in PCT/JP2014/055549 Patent Application No. , dated Apr. 8, 2014.

*Primary Examiner* — Ling Siu Choi
*Assistant Examiner* — Gennadiy Mesh
(74) *Attorney, Agent, or Firm* — Greenblum & Bernstein, P.L.C.

(57) ABSTRACT

Oxygen-absorbing resin composition comprising a polyester containing a constitutional unit (a) comprising tetralin ring structure, for example, an alkyl tetralin dicarboxylate, wherein the alkyl component has, for example, from 2 to 6 carbon atoms, and a constitutional unit (b) derived from a polyfunctional compound, selected from glycerin, trimethylol propane, pentaerythritol, trimellitic acid, trimellitic acid anhydride, pyromellitic acid, and pyromellitic acid anhydride, and a transition metal catalyst.

5 Claims, 2 Drawing Sheets

(56) References Cited

U.S. PATENT DOCUMENTS

| | | |
|---|---|---|
| 2005/0075466 A1* | 4/2005 | Oguro .................... C08L 67/02 |
| | | 525/439 |
| 2014/0225034 A1 | 8/2014 | Okada et al. |
| 2014/0308405 A1 | 10/2014 | Okada et al. |
| 2014/0373485 A1 | 12/2014 | Okada et al. |
| 2015/0090932 A1 | 4/2015 | Okada et al. |
| 2015/0144838 A1 | 5/2015 | Iwanmoto et al. |
| 2015/0232251 A1 | 8/2015 | Ikeda et al. |
| 2015/0259467 A1 | 9/2015 | Iwamoto et al. |
| 2015/0298887 A1 | 10/2015 | Okada et al. |
| 2015/0368022 A1 | 12/2015 | Okada et al. |
| 2016/0009993 A1 | 1/2016 | Ikeda et al. |
| 2016/0017092 A1 | 1/2016 | Iwamoto et al. |
| 2016/0031628 A1 | 2/2016 | Ito et al. |

FOREIGN PATENT DOCUMENTS

| | | |
|---|---|---|
| JP | 5-115776 | 5/1993 |
| JP | 9-234832 | 9/1997 |
| JP | 10-331032 | 12/1998 |
| JP | 2000-212121 | 8/2000 |
| JP | 2001-252560 | 9/2001 |
| JP | 2003-521552 | 7/2003 |
| JP | 2004-131118 | 4/2004 |
| JP | 2011-157411 | 8/2011 |
| JP | 2011-225638 | 11/2011 |
| JP | 2013-129817 | 7/2013 |
| WO | 99/48963 | 9/1999 |
| WO | 1999/061506 | 12/1999 |
| WO | 2013/031877 | 3/2013 |
| WO | 2013/077436 | 5/2013 |

\* cited by examiner

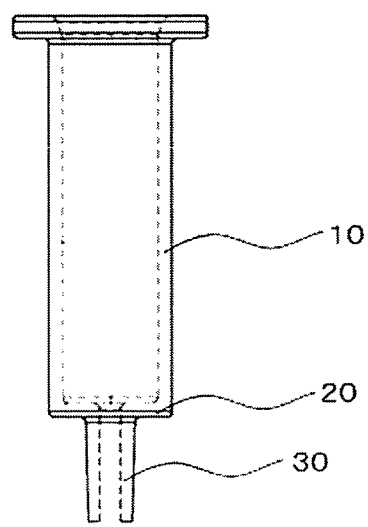
[Figure 1]

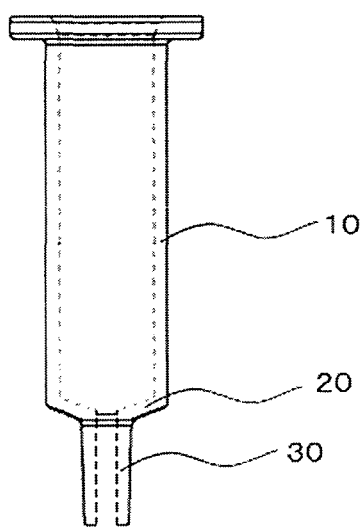
[Figure 2]

OXYGEN-ABSORBING RESIN COMPOSITION

TECHNICAL FIELD

The present invention relates to an oxygen-absorbing resin composition, and particularly to an oxygen-absorbing resin composition at least containing a polyester compound containing a constitutional unit having a tetralin ring and a constitutional unit derived from a polyfunctional (trivalent or more) compound, and a transition metal catalyst.

BACKGROUND ART

Examples of articles which easily deteriorate or degrade under the effect of oxygen include foods, beverages, medicinal products and cosmetics. For the purpose of preventing oxygen oxidation of such articles, thereby storing them for a long term, oxygen absorbents, which remove oxygen within packaging bodies storing these articles, are used.

As the oxygen absorbent, an oxygen absorbent containing an iron powder (hereinafter, referred to also as "iron-based oxygen absorbent") as a reactive base compound is generally used in view of oxygen-absorbing ability, handling and safety. However, the iron-based oxygen absorbent is responsive to a metal detector and thus it is difficult to inspect a foreign matter contained in packaging bodies containing such an iron-based oxygen absorbent, by using a metal detector. Furthermore, since the packaging bodies containing an iron-based oxygen absorbent have a risk of ignition, they cannot be heated by a microwave oven. Moreover, the oxidation reaction of an iron powder requires water, and thus, an oxygen-absorbing effect is exerted only on a preserve rich in moisture content.

Packaging containers are developed by making the container of a multilayered material having an oxygen-absorbing layer formed of an oxygen-absorbing resin composition containing a thermoplastic resin and an iron-based oxygen absorbent, thereby improving a gas barrier property of the container and providing an oxygen-absorbing function to the container itself (see, for example, Patent Document 1). However, this container has the same problems: since an iron-based oxygen absorbent is responsive to a metal detector, a foreign matter cannot be inspected by using a metal detector; heating cannot be made by a microwave oven; and an effect is only exerted on a preserve rich in moisture content. In addition, the container has a problem of opacity, leading to insufficient visibility of content.

In the aforementioned circumstances, it has been desired to develop an oxygen absorbent containing an organic substance as a reactive base compound in place of an iron-based oxygen absorbent. Up to present, as the oxygen absorbent containing an organic substance as a reactive base compound, for example, an oxygen absorbent containing ascorbic acid as a base compound is known (see, for example, Patent Document 2).

In the meantime, an oxygen-absorbing resin composition composed of a resin and a transition metal catalyst is known. For example, a resin composition composed of a polyamide as an oxidizable organic component (in particular, a xylylene group-containing polyamide) and a transition metal catalyst, is known (see, for example, Patent Document 3). In Patent Document 3, articles obtained by molding a resin composition, such as an oxygen absorbent, a packaging material and a multilayer laminate film for packaging are also exemplified.

As an oxygen-absorbing resin composition requiring no moisture content for absorbing oxygen, an oxygen-absorbing resin composition composed of a resin having a carbon-carbon unsaturated bond and a transition metal catalyst, is known (see, for example, Patent Document 4).

As a composition for trapping oxygen, a composition composed of a polymer containing a substituted cyclohexene ring or a low molecular-weight substance bound with the cyclohexene ring and a transition metal is known (see, for example, Patent Document 5).

LIST OF PRIOR ART DOCUMENTS

Patent Documents

Patent Document 1: Japanese Patent Laid-Open No. 09-234832
Patent Document 2: Japanese Patent Laid-Open No. 51-136845
Patent Document 3: Japanese Patent Laid-Open No. 2001-252560
Patent Document 4: Japanese Patent Laid-Open No. 05-115776
Patent Document 5: National Publication of International Patent Application No. 2003-521552

SUMMARY OF INVENTION

Problems to be Solved by Invention

However, the oxygen absorbent composition described in Patent Document 2 has problems in that the oxygen-absorbing performance is primarily low; an effect is exerted only on a preserve rich in moisture content; and the cost is relatively high.

The resin composition described in Patent Document 3 has the following problem. Since an oxygen-absorbing function is exerted by oxidizing a xylylene group-containing polyamide resin in the presence of a transition metal catalyst, the polymer chain of the resin is cut by oxidation degradation after absorption of oxygen, with the result that the strength of the packaging container itself decreases. In addition, the oxygen-absorbing performance of the resin composition described therein is still insufficient and the effect is exerted only on a preserve rich in moisture content.

The oxygen-absorbing resin composition described in Patent Document 4 has the same problem as mentioned above, that is, the polymer chain of the resin is cut by oxidation to produce low molecular-weight organic compounds serving as odor-producing components, with the result that odor is produced after absorption of oxygen.

In the composition described in Patent Document 5, a special material containing a cyclohexene ring must be used. The material still has a problem in relatively easily producing odor.

The present invention was made in consideration of the problems mentioned above. An object of the invention is to provide a novel oxygen-absorbing resin composition not responding to a metal detector, suppressing odor generation and reduction in strength after absorption of oxygen, having excellent oxygen-absorbing performance even in a wide range of humidity conditions from low humidity to high humidity as well as even in the case of a preserve not rich in moisture content, having excellent color tone and appropriate melt viscosity; and containing a polyester compound that can be obtained in a short reaction time.

Means for Solving Problems

The present inventors conducted intensive studies on an oxygen-absorbing resin composition. As a result, they found that the aforementioned problems are solved by using a polyester compound containing a constitutional unit having a predetermined tetralin ring and a constitutional unit derived from a polyfunctional (trivalent or more) compound, and a transition metal catalyst, and accomplished the present invention.

More specifically, the present invention is as follows.

<1> An oxygen-absorbing resin composition at least comprising a polyester compound containing a constitutional unit (a) and a constitutional unit (b), and a transition metal catalyst;

the constitutional unit (a): a constitutional unit having at least one tetralin ring selected from the group consisting of constitutional units represented by the following general formulas (1) to (4):

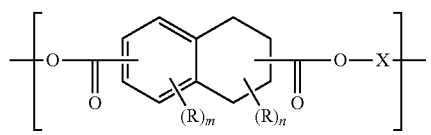
(1)

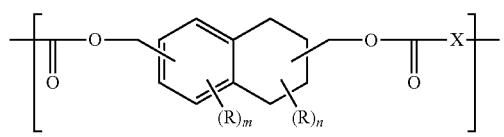
(2)

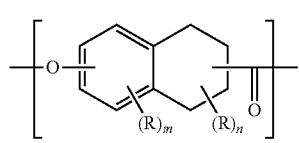
(3)

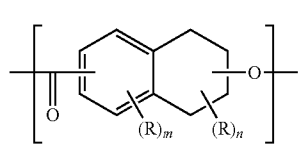
(4)

where R each independently represent a monovalent substituent, which is at least one selected from the group consisting of a halogeno group, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a thiol group, an alkylthio group, an arylthio group, a heterocyclic thio group and an imido group, and which may further have a substituent; where m each independently represent an integer of 0 to 3; where n each independently represent an integer of 0 to 6, at least one hydrogen atom is bound to a benzyl position of a tetralin ring; and where X each independently represent a divalent group containing at least one group selected from the group consisting of an aromatic hydrocarbon group, a saturated or unsaturated alicyclic hydrocarbon group and a linear or branched and saturated or unsaturated aliphatic hydrocarbon group and a heterocyclic group;

constitutional unit (b): a constitutional unit derived from at least one polyfunctional compound selected from the group consisting of a polyvalent (trivalent or more) alcohol, a polyvalent (trivalent or more) carboxylic acid and a derivative thereof and a hydroxycarboxylic acid (trivalence or more) and a derivative thereof.

<2> The oxygen-absorbing resin composition according to the above <1>, wherein
the constitutional unit (a) contains a constitutional unit represented by the general formula (1); and
the molar ratio (constitutional unit (a):constitutional unit (b)) of the constitutional unit (a) to the constitutional unit (b) in the polyester compound is 99.999:0.001 to 95:5.

<3> The oxygen-absorbing resin composition according to the above <1> or <2>, wherein the polyester compound has a melt viscosity value (shear rate: 1216 sec$^{-1}$, temperature: 260° C.) of 80 Pa·sec or more.

<4> The oxygen-absorbing resin composition according to any of the above <1> to <3>, wherein the transition metal catalyst is a catalyst containing at least one transition metal selected from the group consisting of manganese, iron, cobalt, nickel and copper.

<5> The oxygen-absorbing resin composition according to any of the above <1> to <4>, wherein the transition metal catalyst is contained in an amount of 0.001 to 10 parts by mass in terms of a transition metal based on 100 parts by mass of the polyester compound.

<6> The oxygen-absorbing resin composition according to any of the above <1> to <5>, wherein the constitutional unit represented by the general formula (1) is at least one selected from the group consisting of the constitutional units represented by the following formulas (5) to (7):

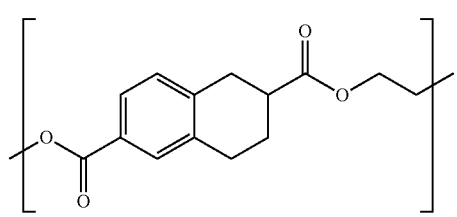
(5)

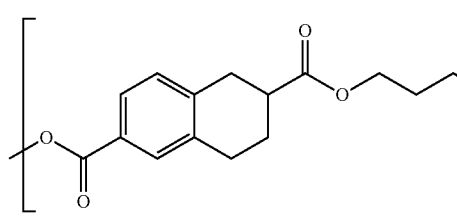
(6)

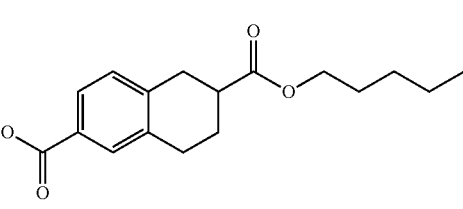
(7)

<7> A molded article containing the oxygen-absorbing resin composition according to any of the above <1> to <6>.

Advantages of Invention

According to the present invention, it is possible to provide an oxygen-absorbing resin composition having excellent oxygen-absorbing performance in a wide range of humidity conditions from low humidity to high humidity and satisfactory molding processability, an oxygen-absorbing multilayer injection molded article using the composition, and an oxygen-absorbing multilayer container. The oxygen-absorbing resin composition of the present invention and molded articles etc. using the composition, since they can absorb oxygen regardless of the presence or absence of the moisture content of a preserve and suppress odor generation after absorption of oxygen as well as suppress reduction in strength, can be applied to a wide variety of uses including foods, cooking foods, beverages, medicinal products and health foods, no matter what products they are. The oxygen-absorbing resin composition of the present invention and molded articles etc. using the composition have an advantage in that they are not responsive to a metal detector. Furthermore, in the present invention, since a polyester compound to be contained in the oxygen-absorbing resin composition can be obtained in a short reaction time, it is possible to provide an oxygen-absorbing resin composition excellent in color tone and molded articles etc. using the composition.

BRIEF DESCRIPTION OF DRAWINGS

FIG. 1 is a sectional view of an oxygen-absorbing multilayer container according to one aspect of the present invention.

FIG. 2 is a sectional view of an oxygen-absorbing multilayer container according to one aspect of the present invention.

MODE FOR CARRYING OUT INVENTION

Hereinafter, an embodiment of the present invention (hereinafter, also described as "the present embodiment") will be described in detail. The following embodiment is illustrative in order to describe the present invention. The present invention is not limited only to the embodiment.

[Oxygen-Absorbing Resin Composition]

The oxygen-absorbing resin composition of the present embodiment at least contains a polyester compound (hereinafter, simply referred also to as "tetralin ring-containing polyester compound") containing a constitutional unit (a) having at least one tetralin ring selected from the group consisting of the constitutional units represented by the above general formulas (1) to (4) and a constitutional unit (b) derived from a polyfunctional (trivalent or more) compound, and a transition metal catalyst.

<Tetralin Ring-Containing Polyester Compound>

The tetralin ring-containing polyester compound to be used in the oxygen-absorbing resin composition of the present embodiment at least contains a constitutional unit (a) having at least one tetralin ring selected from the group consisting of the constitutional units represented by the above general formulas (1) to (4), and a constitutional unit (b) derived from at least one polyfunctional (trivalent or more) compound selected from the group consisting of a polyvalent (trivalent or more) alcohol, a polyvalent (trivalent or more) carboxylic acid and a derivative thereof and a hydroxycarboxylic acid (trivalence or more) and a derivative thereof. The phrase of "contains . . . a constitutional unit" herein means that one or more constitutional units are contained in a compound. It is preferable that such a constitutional unit is contained as a repeat unit in a tetralin ring-containing polyester compound. Likewise, if a tetralin ring-containing polyester compound is a polymer, the compound may be any one of a homopolymer of the above constitutional unit, a random copolymer of the above constitutional unit and another constitutional unit, and a block copolymer of the above constitutional unit and another constitutional unit.

[Constitutional Unit (a)]

The constitutional unit (a) is at least one element of the constitutional units represented by the above general formulas (1) to (4). The constitutional unit (a) preferably contains a constitutional unit represented by the above general formula (1). Moreover, the constitutional unit represented by the above general formula (1) is preferably at least one selected from the group consisting of constitutional units represented by the above formulas (5) to (7). If such a constitutional unit is used, raw material cost tends to be successfully reduced.

In the constitutional units represented by the above general formulas (1) to (4), examples of the monovalent substituent represented by R include, but not particularly limited to, a halogeno group (e.g., a chloro group, a bromo group and an iodo group), an alkyl group (a linear, branched or cyclic alkyl group having preferably 1 to 15 carbon atoms and more preferably 1 to 6 carbon atoms, such as a methyl group, an ethyl group, a n-propyl group, an isopropyl group, a t-butyl group, a n-octyl group, a 2-ethyl hexyl group, a cyclopropyl group and a cyclopentyl group), an alkenyl group (a linear, branched or cyclic alkenyl group having preferably 2 to 10 carbon atoms and more preferably 2 to 6 carbon atoms, such as a vinyl group and an allyl group), an alkynyl group (an alkynyl group having preferably 2 to 10 carbon atoms and more preferably 2 to 6 carbon atoms, such as an ethynyl group and a propargyl group), an aryl group (an aryl group having preferably 6 to 16 carbon atoms and more preferably 6 to 10 carbon atoms, such as a phenyl group and a naphthyl group), a heterocyclic group (a monovalent group obtained by removing a single hydrogen atom from a 5-membered ring or 6-membered ring aromatic or non-aromatic heterocyclic compound having preferably 1 to 12 carbon atoms and more preferably 2 to 6 carbon atoms, such as a 1-pyrazolyl group, a 1-imidazolyl group and a 2-furyl group), a cyano group, a hydroxy group, a carboxyl group, an ester group, an amide group, a nitro group, an alkoxy group (a linear, branched or cyclic alkoxy group having preferably 1 to 10 carbon atoms and more preferably 1 to 6 carbon atoms, such as a methoxy group and an ethoxy group), an aryloxy group (an aryloxy group having preferably 6 to 12 carbon atoms and more preferably 6 to 8 carbon atoms, such as a phenoxy group), an acyl group (including a formyl group; an alkylcarbonyl group having preferably 2 to 10 carbon atoms and more preferably 2 to 6 carbon atoms, an arylcarbonyl group having preferably 7 to 12 carbon atoms and more preferably 7 to 9 carbon atoms, such as an acetyl group, a pivaloyl group and a benzoyl group), an amino group (an alkylamino group having preferably 1 to 10 carbon atoms and more preferably 1 to 6 carbon atoms, an anilino group having preferably 6 to 12 carbon atoms and more preferably 6 to 8 carbon atoms; a heterocyclic amino group having preferably 1 to 12 carbon atoms and more preferably 2 to 6 carbon atoms, such as an amino group, a methylamino group and an anilino group), a thiol group, an alkylthio group (an alkylthio group having preferably 1 to 10 carbon atoms and more preferably 1 to 6 carbon atoms, such as a methylthio group and an ethylthio group), an arylthio group (an arylthio group having preferably 6 to 12 carbon atoms and more preferably 6 to 8 carbon atoms, such as a phenylthio group), a heterocyclic thio group (a heterocyclic thio group having preferably 2 to 10 carbon atoms and more preferably 1 to 6 carbon atoms, such as a 2-benzothiazolyl-thio group) and an imide group (an imide group having preferably 2 to 10 carbon atoms and more preferably 4 to 8 carbon atoms, such as a N-succinimide group and a N-phthalimido group).

Note that when the above monovalent substituent R has a hydrogen atom, the hydrogen atom may be further substituted with a substituent T (herein, substituent T is the same as defined in the above monovalent substituent R). Specific examples thereof include, but not particularly limited to, an alkyl group substituted with a hydroxy group (for example, a hydroxyethyl group), an alkyl group substituted with an alkoxy group (for example, a methoxyethyl group), an alkyl group substituted with an aryl group (for example, a benzyl group), an alkyl group substituted with a primary or secondary amino group (for example, an aminoethyl group), an aryl group substituted with an alkyl group (for example, a p-tolyl group) and an aryloxy group substituted with an alkyl group (for example, a 2-methylphenoxy group). Note that when the monovalent substituent R has a monovalent substituent T, the number of carbon atoms of the substituent T is not included in the number of carbon atoms mentioned above. For example, a benzyl group is regarded as an alkyl group having a single carbon atom substituted with a phenyl group and not regarded as an alkyl group having 7 carbon atoms substituted with a phenyl group. Furthermore, when the above monovalent substituent R has a substituent T, the substituent T may be plural.

In the constitutional units represented by the above general formulas (1) to (4), X represents a divalent group containing at least one group selected from the group consisting of an aromatic hydrocarbon group, a saturated or unsaturated alicyclic hydrocarbon group, a linear or branched and saturated or unsaturated aliphatic hydrocarbon group and a heterocyclic group. The aromatic hydrocarbon group, saturated or unsaturated alicyclic hydrocarbon group, linear or branched and saturated or unsaturated aliphatic hydrocarbon group and heterocyclic group may be substituted or unsubstituted. X may contain a hetero atom or an ether group, a sulfide group, a carbonyl group, a hydroxy group, an amino group, a sulfoxide group or a sulfone group. Herein, examples of the aromatic hydrocarbon group include, but not particularly limited to, an o-phenylene group, a m-phenylene group, a p-phenylene group, a methylphenylene group, an o-xylylene group, a m-xylylene group, a p-xylylene group, a naphthylene group, an anthracenylene group, a phenanthrylene group, a biphenylene group and a fluonylene group. Examples of the alicyclic hydrocarbon group include, but not particularly limited to, cycloalkenylene groups such as a cyclopentylene group, a cyclohexylene group, a methylcyclohexylene group, a cycloheptylene group and a cyclooctylene group; and cycloalkenylene groups such as a cyclohexycenylene group. Examples of the aliphatic hydrocarbon group include, but not particularly limited to, linear or branched alkylene groups such as a methylene group, an ethylene group, a trimethylene group, a propylene group, an isopropylidene group, a tetramethylene group, an isobutylidene group, a sec-butylidene group, a pentamethylene group, a hexamethylene group, a heptamethylene group, an octamethylene group, a nonamethylene group and a dacamethylene group; and alkenylene groups such as a vinylene group, a propenylene group, a 1-butenylene group, a 2-butenylene group, a 1,3-butadienylene group, a 1-pentenylene group, a 2-pentenylene group, a 1-hexenylene group, a 2-hexenylene group and a 3-hexenylene group. Examples of the heterocyclic group include, but not particularly limited to, a five-membered ring containing a single hetero atom, such as a furanyl group, a thiophenyl group and a pyrrolyl group, a six-membered ring containing a single hetero atom, such as a pyridinyl group; a five-membered ring containing two hetero atoms, such as an oxazolyl group and a thiazolyl group; a six-membered ring containing two hetero atoms, such as a pyridazinyl group and a pyrimidinyl group; another five, six and seven-membered ring containing at least one hetero atom; a bicyclic condensed hetero group containing a single hetero atom, such as an indolyl group and a quinolinyl group; a bicyclic condensed hetero group containing two hetero atoms, such as a quinoxalinyl group; a tricyclic condensed hetero group containing a single hetero atom, such as an acridinyl group; a bicyclic condensed hetero group containing two hetero atoms, such as an indazolyl group; and another polycyclic condensed hetero group containing at least one hetero atom. These may further have a substituent. Examples thereof include, but not particularly limited to, a halogeno group, an alkoxy group, a hydroxy group, a carboxyl group, a carboalkoxy group, an amino group, an acyl group, a thio group (for example, an alkylthio group, a phenylthio group, a tolylthio group and a pyridylthio group), an amino group (for example, an unsubstituted amino group, a methylamino group, a dimethylamino group and a phenylamino group), a cyano group and a nitro group.

[Constitutional Unit (b)]

The constitutional unit (b) is a constitutional unit derived from at least one polyfunctional compound of a polyvalent (trivalent or more) alcohol, a polyvalent (trivalent or more) carboxylic acid and a derivative thereof and a hydroxycarboxylic acid (trivalence or more) and a derivative thereof. These polyfunctional compounds can be used alone or in combination with two or more. Due to the content of the constitutional unit (b) derived from a polyfunctional compound, a branched structure can be introduced into a tetralin ring-containing polyester compound to obtain a tetralin ring-containing polyester compound having a higher molecular weight than usual and higher moldability (improved in viscosity). Specific examples of the polyfunctional compound will be described below; however, examples are not particularly limited to these.

Specific examples of the polyvalent (trivalent or more) alcohol include glycerin, trimethylolethane, trimethylol propane, pentaerythritol, 1,2,4-butanetriol, 1,2,5-pentanetriol, 1,2,6-hexanetriol and sorbitol. The polyvalent (trivalent or more) alcohols can be used alone or in combination with two or more.

Specific examples of the polyvalent (trivalent or more) carboxylic acid and a derivative thereof include propane tricarboxylic acid, trimellitic acid, trimellitic acid anhydride, pyromellitic acid, pyromellitic acid anhydride, benzophenone tetracarboxylic acid anhydride, cyclopenta-tetracarboxylic acid anhydride and trimethyl trimellitate. The polyvalent (trivalent or more) carboxylic acids or derivatives thereof can be used alone or in combination with two or more.

Specific examples of the hydroxycarboxylic acid (trivalence or more) and a derivative thereof include malic acid, hydroxyglutaric acid, hydroxymethylglutaric acid, tartaric acid, citric acid, hydroxy isophthalic acid and hydroxyterephthalic acid. The hydroxycarboxylic acids (trivalence or more) can be used alone or in combination with two or more.

As the polyfunctional compound, a polyvalent alcohol or a polyvalent carboxylic acid and a derivative thereof are preferable in view of availability and reactivity. Of them, glycerin, trimethylol propane, pentaerythritol, trimellitic acid, trimellitic acid anhydride, pyromellitic acid and pyromellitic acid anhydride are particularly preferable. These can be used alone or in combination with two or more.

[Method for Producing Tetralin Ring-Containing Polyester Compound]

A tetralin ring-containing polyester compound containing a constitutional unit represented by the above general formula (1) and a constitutional unit (b) can be obtained, for example, by polycondensation of a dicarboxylic acid having a tetralin ring or a derivative (I) thereof, a diol or a derivative (II) thereof, and a polyfunctional compound.

The dicarboxylic acid having a tetralin ring or a derivative (I) thereof is not particularly limited; however, for example, compounds represented by the following general formula (8) are mentioned. The dicarboxylic acids having a tetralin ring or derivatives (I) thereof can be used alone or in combination with two or more.

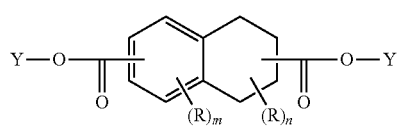

(8)

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group and an imide group, and which may further have a substituent; where m represents an integer of 0 to 3; n represents an integer of 0 to 6, at least one hydrogen atom is bound to the benzyl position of a tetralin ring; where Y each independently represent a hydrogen atom or an alkyl group.

Note that a compound represented by the above general formula (8) can be obtained by reacting, for example, a dicarboxylic acid having a naphthalene ring represented by the following general formula (9) or a derivative thereof with hydrogen.

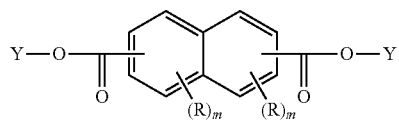

(9)

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group and an imide group, and which may further have a substituent; where m each independently represent an integer of 0 to 3; and where Y each independently represent a hydrogen atom or an alkyl group.

Examples of the diol or a derivative (II) thereof include, but not particularly limited to, ethylene glycol, diethylene glycol, triethylene glycol, polyethylene glycol, propylene glycol, dipropylene glycol, polypropylene glycol, 1,3-propanediol, 2-methyl-1,3-propanediol, 1,3-butanediol, 1,4-butanediol, 1,5-pentanediol, 1,6-hexanediol, 1,7-heptanediol, 1,8-octanediol, 1,9-nonandiol, neopentyl glycol, 1,4-cyclohexanedimethanol, 2-phenylpropanediol, 2-(4-hydroxyphenyl)ethyl alcohol, α,α-dihydroxy-1,3-diisopropylbenzene, α,α-dihydroxy-1,4-diisopropylbenzene, o-xylene glycol, m-xylene glycol, p-xylene glycol, hydroquinone, 4,4-dihydroxyphenyl and naphthalene diol or derivatives of these. Diols or derivatives (II) thereof can be used alone or in combination with two or more.

The tetralin ring-containing polyester compound containing a constitutional unit represented by the above general formula (2) and a constitutional unit (b) can be obtained, for example, by polycondensation of a diol having a tetralin ring or a derivative (III) thereof, a dicarboxylic acid or a derivative (IV) thereof and a polyfunctional compound.

Examples of the diol having a tetralin ring or a derivative (III) thereof include, but not particularly limited to, compounds represented by the following general formula (10). The diol having a tetralin ring or derivatives (III) thereof can be used alone or in combination with two or more.

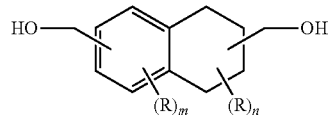

(10)

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group and an imide group, and which may further have a substituent; where m represents an integer of 0 to 3; n represents an integer of 0 to 6, and at least one hydrogen atom is bound to the benzyl position of a tetralin ring.

The compound represented by the above general formula (10) can be obtained by reacting, for example, a diol having a naphthalene ring represented by the following general formula (11) or a derivative thereof with hydrogen.

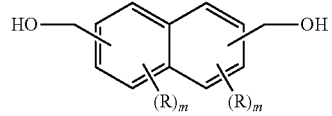

(11)

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group and an imide group, and which may further have a substituent; where m each independently represent an integer of 0 to 3.

Examples of the dicarboxylic acid or a derivative (IV) thereof include, but not particularly limited to, benzene dicarboxylic acids such as oxalic acid, malonic acid, succinic acid, glutaric acid, adipic acid, pimelic acid, suberic acid, azelaic acid, sebacic acid, undecane diacid, dodecane diacid, 3,3-dimethylpentane diacid, phthalic acid, isophthalic acid and terephthalic acid, and naphthalene dicarboxylic acids such as 2,6-naphthalene dicarboxylic acid, anthracene dicarboxylic acid, phenyl malonic acid, phenylene diacetic acid, phenylene dibutyric acid, 4,4-diphenyletherdicarboxylic acid and p-phenylene dicarboxylic acid or derivatives of these. Dicarboxylic acids or derivatives (IV) thereof can be used alone or in combination with two or more.

The tetralin ring-containing polyester compound containing a constitutional unit represented by the above general formula (3) or (4) and a constitutional unit (b) can be obtained by polycondensation of, for example, a hydroxy carboxylic acid having a tetralin ring or a derivative (V) thereof and a polyfunctional compound.

Examples of the hydroxycarboxylic acid having a tetralin ring or a derivative (V) thereof include compounds represented by the following general formula (12) or (13). The hydroxycarboxylic acids having a tetralin ring or derivatives (V) thereof can be used alone or in combination with two or more.

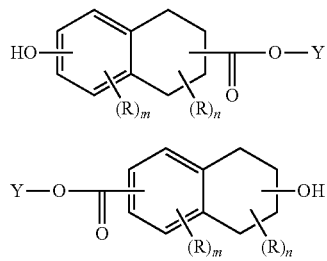

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a thiol group, an alkylthio group, an arylthio group, a heterocyclic thio group and an imido group, and which may further have a substituent; where m represents an integer of 0 to 3; n represents an integer of 0 to 6, and at least one hydrogen atom is bound to the benzyl position of the tetralin ring; where Y each independently represent a hydrogen atom or an alkyl group.

A tetralin ring-containing polyester compound containing a constitutional unit represented by the above general formula (1) or (2) and a constitutional unit (b) can be also obtained, for example, by a hydrogenation reaction of a polyester compound containing a constitutional unit represented by the following general formula (14) or (15) and a constitutional unit (b).

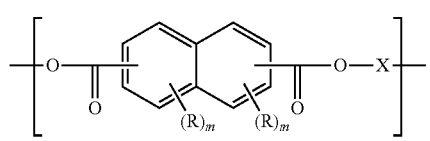

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a thiol group, an alkylthio group, an arylthio group, a heterocyclic thio group and an imido group, and which may further have a substituent; where m each independently represent an integer of 0 to 3; where X represents a divalent group containing at least one group selected from the group consisting of an aromatic hydrocarbon group, a saturated or unsaturated alicyclic hydrocarbon group, a linear or branched and saturated or unsaturated aliphatic hydrocarbon group and a heterocyclic group.

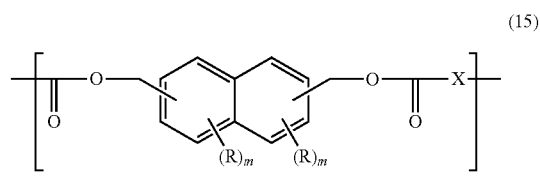

where R each independently represent at least one monovalent substituent, which is selected from the group consisting of a halogeno group, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a thiol group, an alkylthio group, an arylthio group, a heterocyclic thio group and an imido group, and which may further have a substituent; where m each independently represent an integer of 0 to 3; where X represents a divalent group containing at least one group selected from the group consisting of an aromatic hydrocarbon group, a saturated or unsaturated alicyclic hydrocarbon group, a linear or branched and saturated or unsaturated aliphatic hydrocarbon group and a heterocyclic group.

Specific examples of the compounds represented by the above general formulas (8) to (13), the monovalent substituents represented by R and the divalent group represented by X in the constitutional units represented by the above general formulas (14) and (15) are the same as those described in the constitutional units represented by the above general formulas (1) to (4). Thus, repetition of explanation is avoided herein.

The tetralin ring-containing polyester compound to be contained in the oxygen-absorbing resin composition of the present embodiment may contain another constitutional unit having a tetralin ring other than the constitutional units represented by the above general formulas (1) to (4) and a constitutional unit (b) and/or a constitutional unit having no tetralin ring as a copolymerization component(s). Specifically, the compounds mentioned above such as a diol or a derivative (II) thereof and a dicarboxylic acid or a derivative (IV) thereof can be used as the copolymerization component(s). The content ratio of such a copolymerization component, which is not particularly limited as long as the effect of the present embodiment is not excessively damaged, is, for example, preferably 0.01 to 50 mol %, more preferably 0.05 to 30 mol % and further preferably 0.1 to 20 mol %, based on the tetralin ring-containing polyester compound (100 mol %).

As a more preferable compound of the tetralin ring-containing polyester compounds containing a constitutional unit represented by the above general formula (1), for example, tetralin ring-containing polyester compounds containing constitutional units represented by the above formulas (5) to (7) and tetralin ring-containing polyester compounds containing constitutional units represented by the following formulas (16) to (18) are mentioned. In the case of the tetralin ring-containing polyester compounds containing constitutional units represented by the above formulas (5) to (7) and constitutional units represented by the following formulas (16) to (18), raw material cost tends to be successfully reduced.

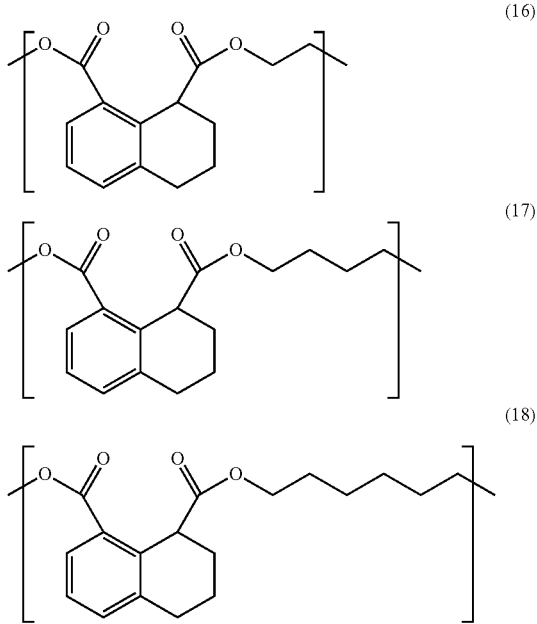

In a tetralin ring-containing polyester compound, the molar ratio (constitutional unit (a):constitutional unit (b)) of the constitutional unit (a) to the constitutional unit (b) is preferably 99.999:0.001 to 95:5, more preferably 99.995:0.005 to 97:3 and particularly preferably 99.99:0.01 to 98:2. If the molar ratio (constitutional unit (a):constitutional unit (b)) of the constitutional unit (a) to the constitutional unit (b) falls within the preferable range, a tetralin ring-containing polyester compound having an appropriate melt viscosity and further suppressing generation of gel can be obtained.

The melt viscosity (shear rate: 1216 sec$^{-1}$, temperature: 260° C.) of the tetralin ring-containing polyester compound is preferably 80 Pa·sec or more and more preferably 100 Pa·sec or more in view of molding processability of a product for practical use. If the melt viscosity falls within the preferable range or more, molding of the tetralin ring-containing polyester compound becomes easier. The upper limit of the melt viscosity is not particularly limited; however, it is, for example, 1000 Pa·sec or less.

Note that, in the present embodiment, the melt viscosity can be measured by the method described in Examples (described later).

The molecular weight of the above tetralin ring-containing polyester compound, which can be appropriately specified in consideration of desired performance, handling property, etc., is not particularly limited. Generally, the weight average molecular weight (Mw) of a tetralin ring-containing polyester compound is preferably $1.0\times10^3$ to $8.0\times10^6$ and more preferably $5.0\times10^3$ to $5.0\times10^6$. Similarly, the number average molecular weight (Mn) of a tetralin ring-containing polyester compound is preferably $1.0\times10^3$ to $1.0\times10^6$ and more preferably $5.0\times10^3$ to $5.0\times10^5$. The molecular weights used herein each refer to a polystyrene equivalent value. Note that, in the present embodiment, the weight average molecular weight and number average molecular weight can be determined by the method described in Examples (described later).

The above tetralin ring-containing polyester compounds can be used alone or in combination with two or more.

Note that the limiting viscosity of a tetralin ring-containing polyester compound, which is not particularly limited, is preferably 0.1 to 2.5 dL/g and more preferably 0.5 to 2.0 dL/g, in view of moldability of the tetralin ring-containing polyester compound. The limiting viscosity herein is represented by the value measured at 25° C. by using a solvent mixture containing phenol and 1,1,2,2-tetrachloro ethane in a mass ratio (phenol:1,1,2,2-tetrachloro ethane) of 6:4.

The glass transition temperature (Tg) of a tetralin ring-containing polyester compound as mentioned above, which is not particularly limited, is preferably 0 to 90° C. and more preferably 10 to 80° C. If the glass transition temperature of a tetralin ring-containing polyester compound falls within the preferable range, pelletization and drying during a production process can be easily performed, compared to the case where the glass transition temperature is outside the range; at the same time, oxygen-absorbing performance tends to be more enhanced. Note that the glass transition temperature herein refers to a value measured by differential scanning calorimetry and can be measured by the method described in Examples (described later).

A method for producing a tetralin ring-containing polyester compound as mentioned above is not particularly limited and any one of methods for producing a polyester conventionally known can be applied. As the method for producing a polyester, a melt polymerization method such as a transesterification method, a direct esterification method, a solution polymerization method or the like is mentioned. Of them, a transesterification method or a direct esterification method is preferable since raw materials are easily obtained.

In producing a tetralin ring-containing polyester compound, a catalyst such as a transesterification catalyst, an esterification catalyst and a polycondensation catalyst, a stabilizer such as an etherification inhibitor, a heat stabilizer and a photo stabilizer, and a polymerization moderator, etc. can be used as long as they are conventionally known. The types and use amounts of these may be appropriately selected depending upon the reaction rate, the molecular weight of a tetralin ring-containing polyester compound, glass transition temperature, viscosity, color tone, safety, heat stability, weather resistance, elution properties themselves, etc. and are not particularly limited. Examples of the catalyst as mentioned above include, but not particularly limited to, compounds of metals such as zinc, lead, cerium, cadmium, manganese, cobalt, lithium, sodium, potassium, calcium, nickel, magnesium, vanadium, aluminum, titanium, antimony and tin (for example, a fatty acid salt, a carbonate, a phosphate, a hydroxide, a chloride, an oxide, and an alkoxide) and magnesium metal. These can be used alone or in combination with two or more.

The above tetralin ring-containing polyester compounds all have hydrogen at the benzyl position of a tetralin ring. Since the hydrogen at the benzyl position is removed by using a tetralin ring-containing polyester compound in combination with a transition metal catalyst as mentioned above, more excellent oxygen absorptivity is exhibited.

The oxygen-absorbing resin composition of the present embodiment can be suppressed in odor generation after absorption of oxygen. The reason is not elucidated; however, for example, the following oxidation reaction mechanism is presumable. In the tetralin ring-containing polyester compound as mentioned above, first hydrogen at the benzyl position of a tetralin ring is removed to produce a radical. The radical then reacts with oxygen to oxidize carbon at the benzyl position. In this manner, a hydroxy group or a ketone group is considered to be produced. In other words, in the oxygen-absorbing resin composition of the present embodiment, a molecular chain of a main oxygen-absorbing component is not cut by an oxidation reaction as is in the prior art; the structure of a tetralin ring-containing polyester compound is maintained; and low molecular weight organic compounds serving as a cause of odor is rarely produced after absorption of oxygen, with the result that odor generation after absorption of oxygen is presumably suppressed to the extent of not externally being detected.

<Transition Metal Catalyst>

As the transition metal catalyst to be used in the oxygen-absorbing resin composition of the present embodiment, any catalyst known in the art can be appropriately selected and used as long as it can serve as a catalyst for the oxidation reaction of a tetralin ring-containing polyester compound as mentioned above. The transition metal catalyst is not particularly limited.

Specific examples of a transition metal catalyst include, but not particularly limited to, organic acid salts, halides, phosphates, phosphites, hypophosphites, nitrates, sulfates, oxides and hydroxides of transition metals. Examples of the transition metal to be contained in the transition metal catalyst include, but not limited to, titanium, vanadium, chromium, manganese, iron, cobalt, nickel, copper, zinc, ruthenium and rhodium. Of them, manganese, iron, cobalt, nickel and copper are preferable in view of catalytic activity to an oxygen absorption reaction. Examples of an organic acid of the organic acid salt include, but not limited to, acetic acid, propionic acid, octanoic acid, lauric acid, stearic acid, acetylacetone, dimethyldithiocarbamic acid, palmitic acid, 2-ethylhexanoic acid, neodecanoic acid, linoleic acid, tall acid, oleic acid, capric acid and naphthenic acid. The transition metal catalyst is preferably a combination of these transition metals and an organic acid, and more preferably a combination of a transition metal such as manganese, iron, cobalt, nickel or copper and an organic acid such as acetic acid, stearic acid, 2-ethylhexanoic acid, oleic acid or naphthenic acid. Note that transition metal catalysts can be used alone or in combination with two or more.

In the oxygen-absorbing resin composition of the present embodiment, the content rate of a tetralin ring-containing polyester compound and a transition metal catalyst, which can be appropriately specified depending upon the types of tetralin ring-containing polyester compound and transition metal catalyst to be used and the desired performances thereof, is not particularly limited. In view of the amount of oxygen absorbed of oxygen-absorbing resin composition, the content of a transition metal catalyst is preferably 0.001 to 10 parts by mass in terms of transition metal based on 100 parts by mass of a tetralin ring-containing polyester compound, and more preferably 0.002 to 2 parts by mass, and further preferably 0.005 to 1 part by mass.

A tetralin ring-containing polyester compound and a transition metal catalyst can be mixed in accordance with a known method in the art. Preferably, they are kneaded by use of an extruder. If so, an oxygen-absorbing resin composition having higher dispersibility can be obtained.

<Additives>

The oxygen-absorbing resin composition of the present embodiment herein may contain additives known in the art other than the aforementioned components as optional components, as long as the effect of the present embodiment is not excessively damaged. Examples of the optional components include, but not particularly limited to, additives such as a drying agent, a pigment such as titanium oxide, a dye, an antioxidant, a slipping agent, an antistatic agent, a plasticizer and a stabilizer; a filler such as calcium carbonate, clay, mica and silica; and a deodorant. The ratio of such additives, which is not particularly limited, is, for example, preferably 0.001 to 50 mass %, more preferably 0.005 to 30 mass % and further preferably 0.01 to 20 mass %.

The oxygen-absorbing resin composition of the present embodiment may further contain a radical generator or a photo initiator, if necessary, in order to facilitate an oxygen absorption reaction. Specific examples of the radical generator include, but not particularly limited to, various types of N-hydroxy imide compounds. Specific examples thereof include, but not particularly limited to, N-hydroxysuccinimide, N-hydroxymaleimide, N,N'-dihydroxycyclohexanetetracarboxydiimide, N-hydroxyphthalimide, N-hydroxytetrachlorophthalimide, N-hydroxytetrabromophthalimide, N-hydroxyhexahydrophthalimide, 3-sulfonyl-N-hydroxyphthalimide, 3-methoxycarbonyl-N-hydroxyphthalimide, 3-methyl-N-hydroxyphthalimide, 3-hydroxy-N-hydroxyphthalimide, 4-nitro-N-hydroxyphthalimide, 4-chloro-N-hydroxyphthalimide, 4-methoxy-N-hydroxyphthalimide, 4-dimethylamino-N-hydroxyphthalimide, 4-carboxy-N-hydroxyhexahydrophthalimide, 4-methyl-N-hydroxyhexahydrophthalimide, N-hydroxyhetimide, N-hydroxyhimimide, N-hydroxytrimellitimide and N,N-dihydroxypyromellitdiimide. Specific examples of the photo initiator include, but not particularly limited to, benzophenone and a derivative thereof, a thiazine dye, a metal porphyrin derivative and an anthraquinone derivative. Note that these radical generators and photo initiators can be used alone or in combination with two or more. The ratio of such a radical generator and photo initiator, which is not particularly limited, is, for example, preferably 0.001 to 10 mass %, more preferably 0.005 to 5 mass % and further preferably 0.01 to 2 mass %.

<Other Thermoplastic Resin>

The oxygen-absorbing resin composition of the present embodiment, if necessary, may further contain another thermoplastic resin other than a tetralin ring-containing polyester compound as mentioned above as long as the effect of the present embodiment is not excessively damaged. If another thermoplastic resin is used in combination, moldability and handling property can be more enhanced.

As another thermoplastic resin, those known in the art can be appropriately used. Specific examples thereof include, but not limited to, polyolefins such as random or block copolymers of α-olefins such as a low-density polyethylene, a medium-density polyethylene, a high-density polyethylene, a linear and low-density polyethylene, a linear and extremely low-density polyethylene, a polypropylene, poly-1-butene, poly-4-methyl-1-pentene or ethylene, propylene, 1-butene, and 4-methyl-1-pentene; acid-modified polyolefins such as maleic anhydride-grafted polyethylene and maleic anhydride-grafted polypropylene; ethylene-vinyl compound copolymers such as an ethylene-vinyl acetate copolymer, an ethylene-vinyl alcohol copolymer, an ethylene-vinyl chloride copolymer, an ethylene-(meth)acrylic acid copolymer, an ion crosslinked product (ionomer) thereof and an ethylene-methyl methacrylate copolymer; styrene resins such as polystyrene, an acrylonitrile-styrene copolymer and an α-methylstyrene-styrene copolymer; polyvinyl compounds such as poly(methyl acrylate) and poly(methyl methacrylate); polyamides such as nylon 6, nylon 66, nylon 610, nylon 12 and poly(metaxylylene adipamide) (MXD6); polyesters such as poly(ethylene terephthalate) (PET), poly(butylene terephthalate) (PBT), poly(trimethylene terephthalate) (PTT), poly(ethylene naphthalate) (PEN), glycol-modified poly(ethylene terephthalate) (PETG), poly(ethylene succinate) (PES), poly(butylene succinate) (PBS), polylactate, polyglycolate, polycaprolactone and polyhydroxyalkanoate; polycarbonates; and polyethers such as polyethylene oxide or mixtures of these. These other thermoplastic resins can be used alone or in combination with two or more.

When the oxygen-absorbing composition of the present embodiment contains another thermoplastic resin, the content rate of the other thermoplastic resin is preferably 10 to 80 parts by mass based on the total amount (100 parts by mass) of the tetralin ring-containing polyester compound and the other thermoplastic resin, in view of oxygen-absorbing performance and moldability, more preferably 15 to 70 parts by mass, and further preferably 20 to 60 parts by mass.
<Usage>

To the oxygen-absorbing resin composition of the present embodiment, a known granulation method or a known molding method such as an extrusion molding can be applied. The composition is molded into, for example, powdery, granular, pellet, film or sheet-forms or other small-piece forms. The oxygen-absorbing resin molded article thus obtained can be used directly as an oxygen absorbent. Alternatively, if the obtained oxygen-absorbing resin molded article is packed in an air-permeable packaging material, the molded article can also be used as an oxygen absorbent packaging body. Furthermore, if the oxygen-absorbing resin composition of the present embodiment is molded into film-form or sheet-form, the molded article can also be used in the form of a label, a card, a packing, etc. Note that a molded article having a thickness of 0.1 to 500 µm is specified as a film, whereas a molded article having a thickness exceeding 500 µm is specified as a sheet.

It is preferable that a pellet-form oxygen-absorbing resin molded article herein is further ground into powdery grains when used in order to increase the contact area with oxygen to thereby effectively deliver oxygen-absorbing performance.

Note that as the air-permeable packaging material, which is not particularly limited, a known packaging material having air permeability can be applied. In view of sufficiently exerting the oxygen absorption effect, an air-permeable packaging material having high air permeability is preferred. Specific examples of the air-permeable packaging material include, but not particularly limited to, highly air-permeable packaging materials used in various usages, including paper sheets such as Japanese paper, machine-made paper and rayon paper; non-woven clothes using various types of fibers obtained from pulp, cellulose and a synthetic resin; a plastic film or a porous plastic film; or a microporous film obtained by adding calcium carbonate etc., followed by drawing it; and a laminate obtained by stacking two types or more selected from these. As the plastic film, laminate films, each formed by laminating and attaching a film of e.g., a polyethylene terephthalate, a polyamide, a polypropylene or a polycarbonate film and a film serving as a sealing film and formed of a polyethylene, an ionomer, a polybutadiene, an ethylene acrylate copolymer, an ethylene methacrylate copolymer or an ethylene vinyl acetate copolymer, can be used.

Note that if the oxygen-absorbing resin composition of the present embodiment is molded into a film form or a sheet form and put in use, it is preferable to form micro voids in the film or the sheet, for example, by drawing. Owing to this operation, the oxygen permeability of the film or sheet to be molded can be enhanced, with the result that the oxygen-absorbing performance of the tetralin ring-containing polyester compound mentioned above tends to be extremely effectively delivered.

The oxygen-absorbing resin composition of the present embodiment molded into a film form or a sheet form can be not only used as a packaging material or a packaging container in the form of a single-layer form but also used in combination with another substrate in the form of a laminate. Typical example of such a laminate is not particularly limited; however, for example, a laminate obtained by stacking at least one layer formed of the oxygen-absorbing resin composition of the present embodiment and at least one layer selected from other resin layers, paper substrate layers or metal foil layers are mentioned. This laminate can be used as an oxygen-absorbing multi-layer packaging material and an oxygen-absorbing multi-layer packaging container. Note that generally, the oxygen-absorbing resin composition (layer) of the present embodiment molded into a film form or a sheet form is preferably provided to an interior side rather than the outer surface of a container etc. so as not to be exposed at the outer surface of the container etc. In view of avoiding direct contact with the content of a container, the oxygen-absorbing resin composition (layer) of the present embodiment molded into a film form or a sheet form is preferably provided outer than the inner surface of the container etc. Likewise, in using the oxygen-absorbing resin composition (layer) of the present embodiment in a multilayer laminate, it is preferable that the composition is molded into a film form or a sheet form and arranged as at least one intermediate layer.

As one preferable aspect of the laminate mentioned above, an oxygen-absorbing multilayer laminate having at least three layers, i.e., a sealant layer containing a thermoplastic resin, an oxygen-absorbing layer containing the oxygen-absorbing resin composition of the present embodiment and a gas barrier layer containing a gas barrier substance, in this order is mentioned. The phrase "having at least three layers in this order" means that the sealant layer, oxygen-absorbing layer and gas barrier layer are arranged in this order; and is a concept including not only an aspect where a sealant layer, an oxygen-absorbing layer and a gas barrier layer are directly stacked (hereinafter, expressed as a "sealant layer/oxygen-absorbing layer/gas barrier layer") but also an aspect where at least one other layer such as a resin layer, a metal foil layer or an adhesive layer are interposed between a sealant layer and an oxygen-absorbing layer or between an oxygen-absorbing layer and a gas barrier layer (hereinafter, referred to as an "intermediate layer") (for example, "sealant layer/resin layer/oxygen-absorbing layer/adhesion layer/gas barrier layer", and "sealant layer/resin layer/adhesion layer/oxygen-absorbing layer/adhesion layer/resin layer/adhesion layer/gas barrier layer/adhesion layer/support") (the same applied hereinafter without an exception).

As another preferable aspect of the laminate mentioned above, an oxygen-absorbing multilayer laminate having at least three layers, i.e., a sealant layer having a polyolefin resin, an oxygen-absorbing layer containing the oxygen-absorbing resin composition of the present embodiment and a gas barrier layer containing a gas barrier substance in this order, is mentioned.

As the thermoplastic resin and polyolefin resin to be used in the sealant layer, it is preferable to be appropriately selected in consideration of compatibility with other layers (oxygen-absorbing layer, gas barrier layer, resin layer, adhesive layer, support, etc.) in adjacent to the sealant layer.

The gas barrier substance to be used as a gas barrier layer is not particularly limited, however, for example, a gas barrier thermoplastic resin, a gas barrier thermosetting resin, silica, alumina, aluminum, etc., (as vapor deposition films) and a metal (as aluminum in the form of foil) can be used. Examples of the gas barrier thermoplastic resin include, but not particularly limited to, an ethylene-vinyl alcohol copolymer, MXD6 and poly(vinylidene chloride). The gas barrier thermosetting resin is not particularly limited, however, a gas barrier epoxy resin, for example, "MAXIVE" manufactured by Mitsubishi Gas Chemical Company, Inc., can be mentioned.

Note that, in consideration of processability of the oxygen-absorbing multilayer laminate as mentioned above in manufacturing, it is preferably to interpose an intermediate layer containing a thermoplastic resin such as a polyolefin resin between a gas barrier layer containing a gas barrier substance and an oxygen-absorbing layer containing the oxygen-absorbing resin composition of the present embodiment. It is preferable that the thickness of the intermediate layer is substantially the same as the thickness of the sealant layer, in view of processability. Herein in consideration of variation by processing, the phrase "substantially the same" means that the ratio of thickness values falls within ±10%.

In the above oxygen-absorbing multilayer laminate, the thickness of the oxygen-absorbing layer, which is not particularly limited, is preferably 5 to 250 μm and more preferably 10 to 150 Ξm. If the thickness of the oxygen-absorbing layer falls within the preferable range, oxygen-absorbing performance tends to be more improved without excessively damaging processability and economic aspect, compared to an oxygen-absorbing layer having a thickness outside the range.

In contrast, in the above oxygen-absorbing multilayer laminate, the thickness of the sealant layer, which is not particularly limited, is preferably 2 to 50 μm and more preferably 5 to 30 μm. If the thickness of the sealant layer falls within the preferable range, the oxygen-absorbing rate of the oxygen-absorbing layer tends to be more enhanced without excessively damaging processability and economic aspect, compared to a sealant layer having a thickness outside the range. Note that in consideration of processability in molding the oxygen-absorbing resin composition of the present embodiment into a film-form or a sheet-form, the thickness ratio of the sealant layer and the oxygen-absorbing layer (the sealant layer: the oxygen-absorbing layer) is preferably 1:0.5 to 1:3 and more preferably 1:1 to 1:2.5.

In the above oxygen-absorbing multilayer laminate, the thickness of the gas barrier layer, which may be appropriately specified depending upon the type of gas barrier substance to be used and gas barrier performance required, is not particularly limited. In view of processability and economic aspect, the thickness of the gas barrier layer in the oxygen-absorbing multilayer laminate is preferably 1 to 100 μm and more preferably 2 to 80 μm.

Note that the above oxygen-absorbing multilayer laminate, if a paper substrate is stacked on the gas barrier layer as the outer layer, can be used as an oxygen-absorbing paper container. In this case, in view of moldability into a paper container, the thickness of the layers inside the gas barrier layer is preferably 100 μm or less, more preferably 80 μm or less, and further preferably 60 μm or less, for example, 50 μm or less.

As a method for manufacturing an oxygen-absorbing multilayer laminate as mentioned above, which is not particularly limited, known methods such as a coextrusion method, a laminating method and a coating method can be applied depending upon e.g., the properties of the material, purpose of processing and processing step. For example, a film or a sheet can be formed by a manufacturing method of extruding a molten resin composition through e.g., a T die and a circular die by an extruder attached therewith or by a method of applying an adhesive to an oxygen-absorbing film or a sheet and adhering it to another film or sheet. Also, if molten resins are simultaneously injected or sequentially injected through multi-layered multiple dies into an injection mold by use of an injector, a multilayer container or a preform for manufacturing a container having a predetermined shape can be formed. The preform is heated to a drawing temperature and stretched in the axial direction and simultaneously stretched in the circumferential direction in accordance with stretch blow-molding by hydrostatic pressure to obtain a bottle.

For example, a film-form oxygen-absorbing multilayer laminate can be further processed into a bag-form or a cover material. For example, a sheet-form oxygen-absorbing multilayer laminate is thermoformed into an oxygen-absorbing multilayer container of a predetermined shape such as a tray, a cup, a bottle and a tube by a molding method such as vacuum molding, air-pressure forming and plug assist molding. The bag-form container and cup-form container thus obtained can be subjected to a boiling treatment performed at 80 to 100° C., a semi-retort treatment, a retort treatment or a high retort treatment performed at 100 to 135° C. The bag-form container, if it is filled with stuff such as food and an open hole is provided, can be preferably used as a pouch for microwave cooking provided with a hole for easily releasing water vapor during microwave cooking.

In using the oxygen-absorbing resin composition of the present embodiment and various types of moldings such as laminates using the composition, initiation of an oxygen absorption reaction can be facilitated and an oxygen-absorbing rate can be increased by irradiation of an energy beam. Examples of the usable energy beam include visible ray, UV ray, X-ray, electron ray and γ ray. The amount of irradiation energy can be appropriately selected depending upon the type of energy line to be used.

As another preferable aspect of the laminate mentioned above, an oxygen-absorbing medical multilayer molded container is mentioned, which has at least three layers, i.e., a first resin layer (layer B) at least containing a thermoplastic resin, an oxygen-absorbing layer (layer A) formed of an oxygen-absorbing resin composition and a second resin layer (layer B) at least containing a thermoplastic resin, in this order.

The layer constitution of the oxygen-absorbing medical multilayer molded container mentioned above is not particularly limited. More specifically, the numbers and types of oxygen-absorbing layers (layer A) and resin layers (layer B) are not particularly limited as long as these layers are arranged in the order of B/A/B. For example, a five-layer (B1/B2/A/B2/B1) structure, which is constituted of one layer A, two layers B1 and two layers B2, may be acceptable. Furthermore, the oxygen-absorbing medical multilayer molded container mentioned above, if necessary, may have an optional layer such as an adhesion layer (layer AD). For example, a seven-layer (B1/AD/B2/A/B2/AD/B1) structure is acceptable.

It is preferable that the thermoplastic resin to be used in layer B is appropriately selected in consideration of compatibility with other layers (oxygen-absorbing layer, gas barrier layer, resin layer, adhesive layer, support, etc.) in adjacent to layer B, the elution into contents, and the like.

As a method for manufacturing the oxygen-absorbing medical multilayer molded container mentioned above, a known method, which varies depending upon the properties of materials, a desired shape, etc. can be applied, but is not particularly limited. For example, the multilayer molded container can be manufactured by applying various types of injection molding methods. A multilayer molded article can be obtained by a method other than the injection molding method, for example, a compression molding method. To the resultant multilayer molded article, secondary processing is applied to mold the article into a container having a desired shape. For example, in a thermoplastic resin melt, an oxygen-absorbing resin composition is provided and the resultant molten lump is supplied to a positive die and simultaneously compressed by a negative die, and then, the compression molded product is cooled and solidified. In this manner, a multilayer molded article can be obtained. As the secondary processing, for example, extrusion molding and compression molding (sheet molding, blow-molding) are applicable.

Usage of the oxygen-absorbing medical multilayer molded container mentioned above is not particularly limited. The container can be used for various uses in various forms. Examples of preferable usage thereof include, but not particularly limited to, vials, ampules, prefilled syringes and vacuum blood collection tubes. Note that, before and after packing of preserves, sterilization treatment can be applied to medical multilayer containers and the preserves, by a method suitable for the preserves. Examples of a sterilization method include a hot water treatment performed at 100° C. or less, a hot water treatment under application of pressure performed at 100° C. or more, thermal sterilization performed at a temperature as high as 121° C. or more, sterilization by electromagnetic wave such as UV ray, microwave and gamma ray, treatment with a gas such as ethylene oxide and sterilization with a chemical agent such as hydrogen peroxide and hypochlorite.

A general prefilled syringe barrel has a male luer taper nozzle by which an injection needle can be connected. A shoulder portion is formed from a base end of the nozzle to a cylinder portion and a flange is formed at the base end of the cylinder portion. The shape of the prefilled syringe barrel is not particularly limited and the prefilled syringe barrel can be molded into a known shape. For example, the shape in accordance with ISO11040-6 shown in FIG. 1 and the shape having an angle larger than 90° as the angle between a body portion 10 and a shoulder portion 20, as shown in FIG. 2, are mentioned. The above angle is preferably larger than 90° and smaller than 125°, more preferably 95° to 120° and further preferably 100° to 115°. If the angle falls within the preferable range, the difference in thickness of the oxygen-absorbing layer can be more reduced when an oxygen-absorbing multilayer prefilled syringe barrel is continuously molded and oxygen-absorbing performance can be stably obtained. For this reason, the angle within the preferable range is favorable.

When a medicinal agent is stored, a nozzle as mentioned above is closed by a cap and a gasket to which a plunger is connected is inserted in the cylinder portion. An oxygen-absorbing prefilled syringe can be manufactured by molding the oxygen-absorbing laminate into the aforementioned barrel shape. As the manufacturing method, a known method which varies depending upon the properties of materials, the desired shape, etc., can be applied. The manufacturing method, which is not particularly limited, is preferably an injection molding method.

More specifically, for example, the following method is mentioned. A predetermined amount of resin constituting layer B is injected into the cavity from the gate provided to the nozzle tip portion of a barrel of a cavity, and subsequently a predetermined amount of resin constituting layer A is injected. The resin constituting layer B previously injected is cooled by the wall surface of the cavity and a core die to form a skin layer; whereas, the resin constituting layer A serves as a core layer, which is to be formed between the skin layers. Thereafter, a predetermined amount of resin constituting layer B is injected again. In this manner, a multilayer injection-molded article serving as a barrel can be manufactured. Herein, it is preferable that the amount of resin constituting layer B to be first injected is adjusted such that layer A is formed closer to the base end of the cylinder portion than the site to which a gasket is to be inserted into the barrel. The oxygen-absorbing layer (layer A) is formed up to the site to which the gasket is to be inserted. In this way, barrier property of the barrel is further ensured. It is also preferable that the amount of resin constituting layer A to be injected is adjusted such that layer A is formed closer to the nozzle tip than the site to be sealed with a cap. The oxygen-absorbing layer (layer A) is formed up to the site to be sealed with a cap. In this way, the barrier property of the barrel is further ensured.

The oxygen-absorbing resin composition of the present embodiment and various types of moldings such as laminates and containers using the composition do not require a moisture content for absorbing oxygen. In other words, oxygen can be absorbed regardless of the presence or absence of the moisture content of a preserve. Thus, the composition and moldings can be used in a wide variety of uses no matter which type of preserve is contained. In particular, odor generation is suppressed after absorption of oxygen, the composition and moldings can be particularly preferably used in e.g., foods, cooking foods, beverages, health foods and medicinal products. More specifically, since the oxygen-absorbing resin composition of the present embodiment and various types of moldings such as laminates using the composition are excellent in oxygen-absorbing performance in a wide range of humidity conditions from low humidity to high humidity (relative humidity 0% to 100%) and excellent in taste and flavor retention property of a content, they are suitable for packaging various articles. In addition, unlike a conventional oxygen-absorbing resin composition using iron powder, the content of iron powder is not essential in the oxygen-absorbing resin composition of the present embodiment. Thus, the iron powder free oxygen-absorbing resin composition does not respond to a metal detector and can be suitably used for a preserve (for example, alcohol beverages and carbonate beverages) which cannot be stored because of the presence of iron.

Specific examples of the preserve include, but not particularly limited to, beverages such as cow milk, juice, coffee, tea and alcohol beverage; liquid seasonings such as source, soy sauce, noodle broth and dressing; cooking foods such as soup, stew and curry; paste foods such as jam and mayonnaise; seafood products such as tuna and fish and shellfish; processed milk products or processed egg products such as cheese, butter and egg; processed livestock products such as meat, salami sausage, sausage and ham; vegetables such as carrot, potato, asparagus and shiitake mushroom; fruits; egg; noodles; rices such as rice and polished rice; cereals such as beans; processed rice foods or processed cereal foods such as steamed rice, festive red rice, rice cake and rice gruel; confectionaries such as adzuki-bean jelly, pudding, cake and steamed bean-jam buns; dry foods (food having a low water activity) such as powdered seasoning, powdered coffee, coffee bean, tea, powdered milk for infants, cooking food for infants, powdered dietary food, nursing care cooking food, dry vegetable, Japanese cracker and rice cracker; chemical products such as an adhesive, a gluing agent, an agrichemical and a pesticide; vitamins such as vitamin A, vitamin B2, vitamin B12, vitamin C, vitamin D, vitamin E, vitamin K; hormonal agents such as alkaloids including atropine, adrenalin and insulin; sugars such as glucose and maltose; antibiotics such as ceftriaxone, cephalosporin and cyclosporine; benzodiazepine medicinal agents such as oxazolam, flunitrazepam, clotiazepam and clobazam; health foods such as a vitamin supplement; pet foods; sundry articles such as a cosmetic, a shampoo, a conditioner and a detergent; and other various articles. Particularly, the oxygen-absorbing resin composition of the present embodiment is suitable for packaging materials for a preserve easily degrading in the presence of oxygen. Examples of such a preserve include beverages beer, wine, fruit juice beverage, fruit juice, vegetable juice, carbonate soft drink and tea; foods such as fruit, nut, vegetable, meat products, infant food, coffee, jam, mayonnaise, ketchup, edible oil, dressing, source, food boiled in soy sauce and milk products; and others such as medicinal products and cosmetics. Note that the term "water activity" refers to a scale showing the content of free water in an article and represented by a numeral from 0 to 1. The article containing no water is represented by 0 and pure water is represented by 1. More specifically, the water activity Aw of an article is defined as follows:

$$Aw = P/P0 = RH/100$$

where P represents a water vapor pressure of a space where an article is sealed and the state of the space reaches equivalent, P0 represents the water vapor pressure of pure water and RH (%) represents the relative humidity of the space.

Note that before and after filling (packaging) of a preserve, the container and the preserve can be sterilized by a method suitable for the preserve. Examples of the sterilization method include heat treatment such as a boiling treatment performed at 100° C. or less, a semi-retort treatment and a retort treat performed at 100° C. or more, and a high retort treatment performed at 130° C. or more; sterilization with an electromagnetic wave such as UV rays, microwave and gamma ray; gas treatment performed with ethylene oxide etc.; and sterilization with a chemical agent such as hydrogen peroxide and hypochlorite.

EXAMPLES

The present invention will be more specifically described by use of Examples and Comparative Examples, below; however, the present invention is not limited by these at all. Note that unless otherwise specified, nuclear magnetic resonance (NMR) measurement was performed at room temperature. In Examples and Comparative Examples, physical property values were measured by the following measurement methods and measurement apparatuses.

(Method for Measuring Glass Transition Temperature)

Glass transition temperature was measured in accordance with JIS K7122. As a measurement apparatus, "DSC-60", manufactured by Shimadzu Corporation was used.

(Method for Measuring Melt Viscosity)

The melt viscosity was measured as follows. A measurement sample was obtained by drying the obtained tetralin ring-containing polyester compound under reduced pressure at a temperature which was 10° C. lower than the glass transition temperature, for 24 hours to thereby remove moisture content. The melt viscosity of the measurement sample was measured by using a capillary rheometer "Capilograph 1D" manufactured by Toyo Seiki Seisaku-sho, Ltd. at a temperature of 260° C. and a shear rate of 1216 sec$^{-1}$.

(Method for Measuring Color Tone (b Value))

b value was measured by using a differential colorimeter "ZE2000" manufactured by NIPPON DENSHOKU INDUSTRIES CO., LTD. The b value represents color tone of blue-yellow (yellow at positive b values and blue at negative b values). The b value is preferably low as long as it is not extremely low.

(Method for Measuring Melting Point)

A melting point was measured in accordance with ISO11357. The peak temperature of the DSC curve obtained by the measurement was specified as the melting point. As a measurement apparatus, "DSC-60" manufactured by Shimadzu Corporation was used.

(Method for Determining Weight Average Molecular Weight and Number Average Molecular Weight)

The weight average molecular weight and number average molecular weight were measured by Gel Permeation Chromatography-low-angle laser light scattering (GPC-LALLS). As a measurement apparatus, "HLC-8320GPC" manufactured by Tosoh Corporation was used.

[Synthesis Example of Monomer]

To an autoclave of 18 L (inner volume), dimethyl naphthalene-2,6-dicarboxylate (2.20 kg), 2-propanol (11.0 kg) and a catalyst (350 g, containing 50 wt % of water) in which palladium (5 wt %) was immobilized on active carbon, were supplied. Subsequently, the air within the autoclave was replaced with nitrogen and the nitrogen was further replaced with hydrogen. Thereafter, hydrogen was supplied to the autoclave until the interior pressure of the autoclave reached 0.8 MPa. Next, a stirrer set in the autoclave was driven and a rotation speed of the stirrer was adjusted to be 500 rpm. After the interior temperature was increased up to 100° C. over 30 minutes while stirring the mixture in the autoclave, hydrogen was further supplied to the autoclave to set the pressure in the autoclave to be 1 MPa. After that, hydrogen was continuously supplied to the autoclave in accordance with pressure reduction with the progression of a reaction so as to maintain 1 MPa. Seven hours later, since pressure reduction within the autoclave was stopped, the autoclave was cooled and unreacted residual hydrogen was released, and then the reaction solution was taken out from the autoclave. After the reaction solution was filtered to remove the catalyst, 2-propanol was distilled away from the separated filtrate by an evaporator to obtain a crude product. To the crude product obtained, 2-propanol (4.40 kg) was added. Dimethyl tetralin-2,6-dicarboxylate was purified by recrystallization in a yield of 80%. Note that NMR analysis results were as follows. 1H-NMR (400 MHz CDCl3) δ7.76-7.96 (2H m), 7.15 (1H d), 3.89 (3H s), 3.70 (3H s), 2.70-3.09 (5H m), 1.80-1.95 (1H m).

Example 1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in the above Synthesis Example of monomer, ethylene glycol (217 g), glycerin (1.6 g) as a polyfunctional compound, tetrabutyl titanate (0.038 g) and zinc acetate (0.15 g) were supplied. The temperature of the mixture in the apparatus was raised up to 230° C. under a nitrogen atmosphere to perform a transesterification reaction. After the reaction conversion rate of the dicarboxylic acid component reached 90% or more, the temperature was gradually increased and pressure was gradually decreased over 90 minutes and then polycondensation was performed at 260° C. and 133 Pa or less for one hour to obtain a tetralin ring-containing polyester compound (1) (hereinafter referred to also as "polyester compound (1)").

The weight average molecular weight and number average molecular weight of the polyester compound (1) obtained were determined by the aforementioned methods. As a result, the polystyrene-equivalent weight average molecular weight was $7.0 \times 10^4$ and the number average molecular weight thereof was $3.0 \times 10^4$. The glass transition temperature and melting point of the polyester compound (1) were measured by the aforementioned methods. As a result, the glass transition temperature was 69° C. and the melting point was not determined because of amorphous crystal. In addition, the b value and melt viscosity of the polyester compound (1) were measured by the aforementioned methods. These results are shown in Table 1.

With the obtained polyester compound (1) (100 parts by mass), cobalt stearate (II) (0.02 parts by mass in terms of cobalt) was dry-blended to obtain an oxygen-absorbing resin composition. The obtained oxygen-absorbing resin composition was formed into a film by use of a double-screw extruder having two screws of 20 mm in diameter at an extrusion temperature of 240° C., a screw rotation number of 60 rpm, a feed screw rotation number of 16 rpm and a haul-off speed of 1.3 m/min. In this manner, an oxygen-absorbing film having a width of 130 mm and a thickness of 95 to 105 μm was manufactured.

Next, two gas barrier bags formed of an aluminum foil laminate film were prepared. Two test pieces (100 mm in length×100 mm in width) of the obtained oxygen-absorbing film were put in the two gas barrier bags together with 500 cc of air. The relative humidity in one of the gas barrier bags was adjusted to be 100%; whereas the relative humidity of the other gas barrier bag was adjusted to be 30% and then the gas barrier bags were separately sealed to obtain sealed bags. The sealed bags thus obtained were stored at 40° C. for 7 days. The total amount of oxygen absorbed (hereinafter, referred to also as "amount of oxygen absorbed") by the oxygen-absorbing film during this period was measured. The amount of oxygen absorbed was measured by an oximeter (trade name: LC-750F, manufactured by Toray Industries, Inc.).

Furthermore, sealed bags were manufactured in the same manner such that the relative humidity of the gas barrier bags was adjusted to be 100%. The sealed bags manufactured were stored at 40° C. and a relative humidity of 100% for one month. Appearance of the oxygen-absorbing films after storage for one month was visually checked; at the same time, odor when the sealed bags were opened was checked. These results are shown in Table 1.

Example 2

A tetralin ring-containing polyester compound (2) (hereinafter referred to also as "polyester compound (2)") was synthesized in the same manner as in Example 1 except that the content of glycerin was 3.2 g. The obtained polyester compound (2) had a polystyrene-equivalent weight average molecular weight of $8.0 \times 10^4$, a number average molecular weight of $3.1 \times 10^4$ and a glass transition temperature of 67° C. The melting point of the polyester compound (2) was not determined because of amorphous crystal. Furthermore, the b value and melt viscosity of the polyester compound (2) were measured by the aforementioned methods. Moreover, an oxygen-absorbing film was manufactured in the same manner as in Example 1 except that the polyester compound (2) was used in place of the polyester compound (1). The amount of oxygen absorbed was measured, appearance was visually checked, and odor was checked. These results are shown in Table 1.

Example 3

A tetralin ring-containing polyester compound (3) (hereinafter referred to also as a "polyester compound (3)") was synthesized in the same manner as in Example 1 except that pentaerythritol (0.95 g) was used in place of glycerin. The obtained polyester compound (3) had a polystyrene-equivalent weight average molecular weight of $7.1 \times 10^4$, a number average molecular weight of $3.4 \times 10^4$ and a glass transition temperature of 68° C. The melting point of the polyester compound (3) was not determined because of amorphous crystal. Furthermore, the b value and melt viscosity of the polyester compound (3) were measured by the aforementioned methods. Moreover, an oxygen-absorbing film was manufactured in the same manner as in Example 1 except that the polyester compound (3) was used in place of the polyester compound (1). The amount of oxygen absorbed was measured, appearance was visually checked, and odor was checked. These results are shown in Table 1.

Example 4

A tetralin ring-containing polyester compound (4) (hereinafter referred to also as "polyester compound (4)") was synthesized in the same manner as in Example 1 except that trimellitic acid (2.3 g) was used in place of glycerin. The obtained polyester compound (4) had a polystyrene-equivalent weight average molecular weight of $6.9 \times 10^4$, a number average molecular weight of $3.0 \times 10^4$ and a glass transition temperature of 70° C. The melting point of the polyester compound (4) was not determined because of amorphous crystal. Furthermore, the b value and melt viscosity of the polyester compound (4) were measured by the aforementioned methods. Moreover, an oxygen-absorbing film was manufactured in the same manner as in Example 1 except that the polyester compound (4) was used in place of the polyester compound (1). The amount of oxygen absorbed was measured, appearance was visually checked, and odor was checked. These results are shown in Table 1.

Example 5

A tetralin ring-containing polyester compound (5) (hereinafter referred to also as "polyester compound (5)") was synthesized in the same manner as in Example 1 except that the content of ethylene glycol was 150 g and 1,4-butane diol (93 g) was further added. In the polyester compound (5), the molar ratio (ethylene glycol:1,4-butane diol) of ethylene glycol to 1,4-butane diol was 60:40. The polyester compound (5) had a polystyrene-equivalent weight average molecular weight of $7.5 \times 10^4$, a number average molecular weight of $3.2 \times 10^4$ and a glass transition temperature of 56° C. The melting point of the polyester compound (5) was not determined because of amorphous crystal. Furthermore, the b value and melt viscosity of the polyester compound (5) were measured by the aforementioned methods. Moreover, an oxygen-absorbing film was manufactured in the same manner as in Example 1 except that the polyester compound (5) was used in place of the polyester compound (1). The amount of oxygen absorbed was measured, appearance was visually checked, and odor was checked. These results are shown in Table 1.

Comparative Example 1

A polyester compound (6) was synthesized in the same manner as in Example 1 except that glycerin was not added. The polyester compound (6) had a polystyrene-equivalent weight average molecular weight of $4.9 \times 10^4$, a number average molecular weight of $2.4 \times 10^4$ and a glass transition temperature of 56° C. The melting point of the polyester compound (6) was not determined because of amorphous crystal. Furthermore, the b value and melt viscosity of the polyester compound (6) were measured by the aforementioned methods. Moreover, an oxygen-absorbing film was manufactured in the same manner as in Example 1 except that the polyester compound (6) was used in place of the polyester compound (1). The amount of oxygen absorbed was measured, appearance was visually checked, and odor was checked. These results are shown in Table 1.

Comparative Example 2

A polyester compound (7) was synthesized in the same manner as in Example 5 except that glycerin was not added. The polyester compound (7) had a polystyrene-equivalent weight average molecular weight of $5.0 \times 10^4$, a number average molecular weight of $2.4 \times 10^4$ and a glass transition temperature of 56° C. The melting point of the polyester compound (7) was not determined because of amorphous crystal. Furthermore, the b value and melt viscosity of the polyester compound (7) were measured by the aforementioned methods. Moreover, an oxygen-absorbing film was manufactured in the same manner as in Example 1 except that the polyester compound (7) was used in place of the polyester compound (1). The amount of oxygen absorbed was measured, appearance was visually checked, and odor was checked. These results are shown in Table 1.

TABLE 1

| | Resin used in oxygen-absorbing resin composition | | Physical property of resin | | Amount of oxygen absorbed[3] | | | |
|---|---|---|---|---|---|---|---|---|
| | Type | Polyfunctional compound | Amount added[1] (mol %) | Melt viscosity[2] (Pa · sec) | b Value | 100% Humidity | 30% Humidity | Appearance[4] | Odor[4] |
| Example 1 | Polyester compound (1) | Glycerin | 0.5 | 164.2 | 4.77 | 20 cc | 19 cc | Shape is maintained | None |
| Example 2 | Polyester compound (2) | Glycerin | 1.0 | 159.6 | 4.60 | 18 cc | 21 cc | Shape is maintained | None |
| Example 3 | Polyester compound (3) | Pentaerythritol | 0.2 | 168.2 | 4.87 | 21 cc | 20 cc | Shape is maintained | None |
| Example 4 | Polyester compound (4) | Trimellitic acid | 0.5 | 162.6 | 5.02 | 20 cc | 20 cc | Shape is maintained | None |
| Example 5 | Polyester compound (5) | Glycerin | 0.5 | 149.3 | 3.46 | 25 cc | 24 cc | Shape is maintained | None |
| Comparative Example 1 | polyester compound (6) | — | 0 | 78.7 | 5.53 | 19 cc | 20 cc | Shape is maintained | None |
| Comparative Example 2 | Polyester compound (7) | — | 0 | 65.3 | 3.04 | 23 cc | 24 cc | Shape is maintained | None |

[1] Content of polyfunctional compound per mole of constitutional unit (a)
[2] Melt viscosity at 260° C. at a shear rate of 1216 sec$^{-1}$
[3] Total amount of oxygen absorbed during 7 days from initiation of test
[4] Evaluated after storage for one month at 40° C. and a humidity of 100%

As is apparent from Table 1, it was confirmed that the oxygen-absorbing resin compositions of the present embodiment delivered satisfactory oxygen-absorbing performance both in high humidity and low humidity conditions. It was also confirmed that the polyester compound to be used in the present embodiment, even if it is produced in a short polycondensation time, has satisfactory melt viscosity and color tone. Moreover, the oxygen-absorbing film obtained from the oxygen-absorbing resin composition of the present embodiment maintained the shape of the film without being collapsed even after absorption of oxygen and no odor was sensed.

Example 6

[Manufacturing of Oxygen-Absorbing Multilayer Syringe]

Using an injection molding machine (mode: ASB-12N/10, manufactured by Nissei ASB Machine Co., Ltd.), two syringes different in shape, i.e., oxygen-absorbing multilayer syringes 1 and 2 (hereinafter referred to also as "syringe 1" and "syringe 2", respectively) were manufactured in the following conditions. First, the thermoplastic resin for constituting a resin layer (layer B) was injected from an injection cylinder and then the oxygen-absorbing resin composition for constituting an oxygen-absorbing layer (layer A) was injected from another injection cylinder simultaneously with the thermoplastic resin for constituting layer B. Subsequently, the thermoplastic resin for constituting layer B was injected in a necessary amount to fill the cavity of an injection mold to manufacture a syringe constituted of three layers (B/A/B). As the oxygen-absorbing resin composition for constituting layer A, a resin composition obtained by dry blending cobalt stearate (II) (0.02 parts by mass in terms of cobalt) with the polyester compound (1) (100 parts by mass) obtained in Example 1 was used. The mass ratio of layer A was specified as 30 mass % of the total mass of the syringe. A cycloolefin copolymer (trade name: "TOPAS 6013" (hereinafter abbreviated also as "COC") manufactured by Ticona GmbH) was used as the thermoplastic resin for constituting layer B.

(Shape of Syringe 1)

Syringe 1 was a standard type (a content of 1 cc) formed in accordance with ISO11040-6 and having the shape shown in FIG. 1.

(Shape of Syringe 2)

Syringe 2 had the same shape (as shown in FIG. 2) as in syringe 1 except that the thickness of a body portion 10 was 1.6 mm, the angle formed between the body portion 10 and the shoulder portion 20 was 110° and the exterior angle between the shoulder portion 20 and the needle contact portion 30 was 110°.

(Conditions for Molding Syringe)

Temperature of injection cylinder for layer A: 220 to 260° C.

Temperature of injection cylinder for layer B: 280° C.

Temperature of resin flow channel in injection mold: 260 to 280° C.

Mold temperature: 18° C.

[Evaluation of Syringe Moldability]

Two syringes different in shape were continuously manufactured and the moldability was evaluated as follows. The results are shown in Table 2.

⊚: Constitution of three layers is not disturbed in continuous molding and the range of molding condition for providing an oxygen-absorbing layer having stable thickness is broad.

○: Constitution of three layers is not disturbed in continuous molding and the range of molding condition for providing an oxygen-absorbing layer having stable thickness is narrow.

Δ: Constitution of three layers is sometimes disturbed in continuous molding and the range of molding condition for providing an oxygen-absorbing layer having stable thickness is narrow.

x: Constitution of three layers is frequently disturbed in continuous molding and the range of molding condition for providing an oxygen-absorbing layer having stable thickness is narrow.

Examples 7 to 10, Comparative Examples 3 and 4

Oxygen-absorbing multilayer syringes were continuously manufactured in the same manner as in Example 6 except that polyester compounds shown in Table 2 were used in place of the polyester compound (1), and moldability was evaluated. The results are shown in Table 2.

TABLE 2

| | Resin used in oxygen-absorbing resin composition | | | Physical property of resin | | Moldability[3] | |
|---|---|---|---|---|---|---|---|
| | Type | Polyfunctional compound | Amount added[1] (mol %) | Melt viscosity[2] (Pa · sec) | b Value | Syringe 1 | Syringe 2 |
| Example 6 | Polyester compound (1) | Glycerin | 0.5 | 164.2 | 4.77 | ○ | ⊚ |
| Example 7 | Polyester compound (2) | Glycerin | 1.0 | 159.6 | 4.60 | ○ | ⊚ |
| Example 8 | Polyester compound (3) | Pentaerythritol | 0.2 | 168.2 | 4.87 | ○ | ○ |
| Example 9 | Polyester compound (4) | Trimellitic acid | 0.5 | 162.6 | 5.02 | ○ | ⊚ |
| Example 10 | Polyester compound (5) | Glycerin | 0.5 | 149.3 | 3.46 | ○ | ⊚ |
| Comparative Example 3 | Polyester compound (6) | — | 0 | 78.7 | 5.53 | Δ | ○ |
| Comparative Example 4 | Polyester compound (7) | — | 0 | 65.3 | 3.04 | x | ○ |

[1]Content of polyfunctional compound per mole of constitutional unit (a)
[2]Melt viscosity at 260° C. at a shear rate of 1216 sec$^{-1}$
[3]⊚: Constitution of three layers is not disturbed and the range of molding condition for providing an oxygen-absorbing layer having stable thickness is broad.
○: Constitution of three layers is not disturbed and the range of molding condition for providing an oxygen-absorbing layer having stable thickness is narrow.
Δ: Constitution of three layers is sometimes disturbed and the range of molding condition for providing an oxygen-absorbing layer having stable thickness is narrow.
x: Constitution of three layers is frequently disturbed and the range of molding condition for providing an oxygen-absorbing layer having stable thickness is narrow.

As is apparent from Table 2, the oxygen-absorbing multilayer syringe manufactured by using the oxygen-absorbing resin compositions of the present embodiment had no disturbance in constitution of three layers in continuous molding. Particularly, it was demonstrated that if the shape of syringe 2 is employed, the range of molding condition for providing the oxygen-absorbing layer having stable thickness becomes broad.

As described in the foregoing, the present invention is not limited to the above embodiment and Examples and can be appropriately modified within the gist of the invention.

INDUSTRIAL APPLICABILITY

The oxygen-absorbing resin composition of the present invention and a molded article thereof have excellent oxygen-absorbing performance in a wide range of humidity conditions from low humidity to high humidity. The polyester compound to be contained in the oxygen-absorbing resin composition of the present invention has satisfactory melt viscosity and color tone even if it is produced in short polycondensation time. Accordingly, the oxygen-absorbing resin composition of the present invention and a molded article thereof can be widely and effectively used in the general technical field in which oxygen absorption is required, and in particular, can be particularly effectively used in the field in which high moldability and highly accurate dimension are required. Furthermore, the oxygen-absorbing resin composition of the present invention and the molded article thereof can absorb oxygen regardless of the presence or absence of moisture content in a preserve, and suppress odor generation after absorption of oxygen. Thus, they can be widely and effectively used in e.g., foods, cooking foods, beverages, medicinal products and health foods. In addition, since the present invention can realize an oxygen-absorbing resin composition and a molded article thereof, which are not responsive to a metal detector, they can be widely and effectively applied to uses requiring external inspection of metals, metal pieces, etc. by a metal detector, for example, packaging materials and containers.

REFERENCE SIGNS LIST

10: Body portion
20: Shoulder portion
30: Needle contact portion

The invention claimed is:

1. An oxygen-absorbing resin composition at least comprising a polyester compound containing a constitutional unit (a) and a constitutional unit (b), and a transition metal catalyst;

the constitutional unit (a): a constitutional unit having at least one tetralin ring selected from the group consisting of constitutional units represented by the following general formulas (5) to (7):

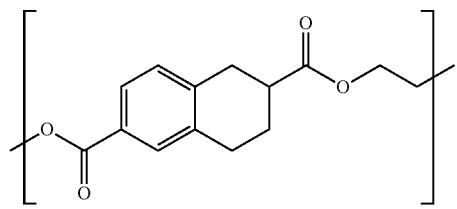
(5)

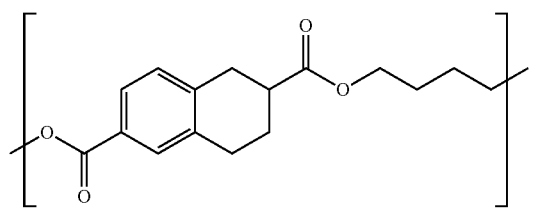
(6)

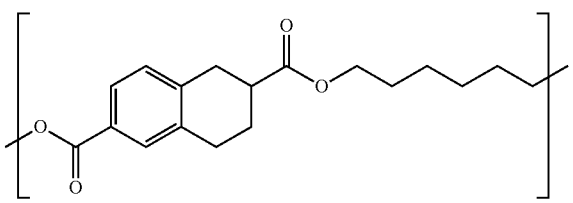
(7)

and
constitutional unit (b): a constitutional unit derived from a polyfunctional compound selected from at least one of glycerin, trimethylol propane, pentaerythritol, trimellitic acid, trimellitic acid anhydride, pyromellitic acid, and pyromellitic acid anhydride, wherein the oxygen-absorbing resin composition further comprises a catalyst for producing the polyester compound, and wherein the transition metal catalyst is different from the catalyst for producing the polyester compound, and wherein the content of component (b) is from 0.2 mol % to 1 mol % and the polyester compound optionally contains up to 0.1 mol % of constitutional units other than constitutional units (a) and (b), and the sum of all constitutional units is 100 mol %, and wherein the content of the polyester compound is at least 90% by mass based on a total amount of the oxygen-absorbing resin composition.

2. The oxygen-absorbing resin composition according to claim 1, wherein the polyester compound has a melt viscosity value (shear rate: 1216 sec-1, temperature: 260° C.) of 80 Pa·sec or more.

3. The oxygen-absorbing resin composition according to claim 1, wherein the transition metal catalyst is a catalyst comprising at least one transition metal selected from the group consisting of manganese, iron, cobalt, nickel and copper.

4. The oxygen-absorbing resin composition according to claim 1, wherein the transition metal catalyst is contained in an amount of 0.001 to 10 parts by mass in terms of a transition metal based on 100 parts by mass of the polyester compound.

5. A molded article comprising the oxygen-absorbing resin composition according to claim 1.

* * * * *